(12) United States Patent
Buckland et al.

(10) Patent No.: US 7,869,663 B2
(45) Date of Patent: Jan. 11, 2011

(54) METHODS, SYSTEMS AND COMPUTER PROGRAM PRODUCTS FOR ANALYZING THREE DIMENSIONAL DATA SETS OBTAINED FROM A SAMPLE

(75) Inventors: Eric L. Buckland, Hickory, NC (US); William J. Brown, Durham, NC (US); Joseph A. Izatt, Raleigh, NC (US)

(73) Assignee: Bioptigen, Inc., Durham, NC (US)

( * ) Notice: Subject to any disclaimer, the term of this patent is extended or adjusted under 35 U.S.C. 154(b) by 1119 days.

(21) Appl. No.: 11/461,083

(22) Filed: Jul. 31, 2006

(65) Prior Publication Data

US 2007/0025642 A1 Feb. 1, 2007

Related U.S. Application Data

(60) Provisional application No. 60/704,343, filed on Aug. 1, 2005.

(51) Int. Cl.
 *G06K 9/00* (2006.01)
 *G06K 9/36* (2006.01)
 *G06K 9/32* (2006.01)
(52) U.S. Cl. .................. 382/294; 382/131; 382/287; 382/289; 382/295; 382/296
(58) Field of Classification Search ............ None
 See application file for complete search history.

(56) References Cited

U.S. PATENT DOCUMENTS

| | | | |
|---|---|---|---|
| 4,580,219 A * | 4/1986 | Pelc et al. .................. 382/131 |
| 5,150,421 A | 9/1992 | Morishita et al. | |
| 5,204,627 A | 4/1993 | Mistretta et al. | |
| 5,226,113 A | 7/1993 | Cline et al. | |
| 5,233,299 A | 8/1993 | Souza et al. | |
| 5,297,551 A | 3/1994 | Margosian et al. | |
| 5,368,033 A | 11/1994 | Moshfeghi | |
| 5,760,781 A | 6/1998 | Kaufman et al. | |
| 5,852,646 A * | 12/1998 | Klotz et al. .................. 378/8 |

(Continued)

OTHER PUBLICATIONS

Choma et al., "Sensitivity advantage of swept source and Fourier domain optical coherence tomography," Optics Express, vol. 11, No. 18, Sep. 8, 2003, 2183-2189.

(Continued)

*Primary Examiner*—Vikkram Bali
*Assistant Examiner*—Michelle Entezari
(74) *Attorney, Agent, or Firm*—Myers Bigel Sibley & Sajovec

(57) ABSTRACT

Methods of analyzing three dimensional data sets obtained from a sample over time are provided. A first three dimensional data set is obtained from the sample at a first time. A first volume intensity projection (VIP) image is created from the first three dimensional data set. One or more first landmarks are identified and registered in the first VIP image. A second three dimensional data set is obtained from the sample at a second time, different from the first time. A second VIP image is created from the second three dimensional data set. The one ore more first landmarks are identified and registered in the second VIP image. The first and second VIP images are aligned based on the registered one or more first landmarks in the first and second VIP images. Related systems and computer program products are also provided.

38 Claims, 11 Drawing Sheets

U.S. PATENT DOCUMENTS

| | | | |
|---|---|---|---|
| 6,102,864 A | 8/2000 | Hatfield et al. | |
| 6,436,049 B1 | 8/2002 | Kamiyama et al. | |
| 6,459,094 B1 * | 10/2002 | Wang et al. | 250/584 |
| 6,490,335 B1 * | 12/2002 | Wang et al. | 378/15 |
| 6,519,354 B1 | 2/2003 | Oshio | |
| 6,671,538 B1 * | 12/2003 | Ehnholm et al. | 600/425 |
| 6,885,764 B2 * | 4/2005 | Wang et al. | 382/131 |
| 6,904,163 B1 | 6/2005 | Fujimura et al. | |
| 6,907,281 B2 * | 6/2005 | Grzeszczuk | 600/407 |
| 7,020,318 B2 | 3/2006 | Oshio et al. | |
| 7,170,517 B2 | 1/2007 | Raman et al. | |
| 7,301,644 B2 | 11/2007 | Knighton et al. | |
| 7,505,142 B2 | 3/2009 | Knighton et al. | |
| 7,532,750 B2 * | 5/2009 | Sasaki et al. | 382/154 |
| 7,623,736 B2 * | 11/2009 | Viswanathan | 382/293 |
| 2001/0036303 A1 * | 11/2001 | Maurincomme et al. | 382/132 |
| 2004/0215071 A1 * | 10/2004 | Frank et al. | 600/407 |
| 2005/0018201 A1 | 1/2005 | de Boer et al. | |
| 2005/0065421 A1 * | 3/2005 | Burckhardt | 600/407 |
| 2005/0111720 A1 * | 5/2005 | Gurcan et al. | 382/131 |
| 2005/0140984 A1 | 6/2005 | Hitzenberger | |
| 2005/0226375 A1 * | 10/2005 | Eberhard et al. | 378/62 |
| 2006/0030768 A1 * | 2/2006 | Ramamurthy et al. | 600/407 |
| 2007/0002327 A1 | 1/2007 | Zhou et al. | |
| 2007/0003117 A1 * | 1/2007 | Wheeler et al. | 382/128 |
| 2007/0291277 A1 | 12/2007 | Everett et al. | |

OTHER PUBLICATIONS

Dorrer et al., "Spectral resolution and sampling issues in Fourier-transformation spectral interferometry," J. Opt. Soc. Am. B, vol. 17, No. 10, Oct. 2000, 1795-1802.

Häusler et al., "'Coherence Radar' and 'Spectral Radar'—New Tools for Dermatological Diagnosis," Journal of Biomedical Optics, vol. 3, No. 1, Jan. 1998, 21-31.

Jiao et al., "Simultaneous acquisition of sectional and fundus ophthalmic images with spectral-domain optical coherence tomography," Optics Express, Vo. 13, No. 2, Jan. 24, 2005, 444-452.

Leitgeb et al., "Performance of fourier domain vs. time domain optical coherence tomography," Optics Express, vol. 11, No. 8, Apr. 21, 2003, 889-894.

Tan-no et al., "Optical multimode frequency-domain reflectometer," Optics Letters, vol. 19, No. 8, Apr. 15, 1994, 587-589.

Yun et al., "High-speed spectral-domain optical coherence tomography at 1.3 μm wavelength," Optics Express, vol. 11, No. 26, Dec. 29, 2003, 3598-3604.

International Search Report and Written Opinion for PCT/US2006/029535; date of mailing Aug. 22, 2007.

Mahmoud et al. "Comparison of three methods for registration of abdominal/pelvic volume data sets from functional-anatomic scans" *Proc. of SPIE* 3979 1378.

Srinivasan et al. "Three-dimensional retinal imaging with ultrahigh resolution, Fourier/spectral domain optical coherence tomography" *Proc. of SPIE* 5688(1):90-99 (2005).

Jiao et al., "Registration of high-density cross sectional images to the fundus image in spectral-domain ophthalmic optical coherence tomography," Optics Express, vol. 14, No. 8, Apr. 17, 2006, 3368-3376.

Bruckner, Stefan, "Introduction to Scientific Visualization," Simon Fraser University/Vienna University of Technology, Applicants' Admitted Prior Art, 17 pages.

Kaufman et al., "Real-Time Volume Rendering," to appear in the International Journal of Imaging Systems and Technology, special issue on 3D Imaging, Center for Visual Computing (CVC) and Department of Computer Science, State University of New York at Stony Brook, Applicants' Admitted Prior Art, 9 pages.

Heidrich et al., "Interactive Maximum Projection Volume Rendering," Sixth IEEE Visualization 1995 (VIS '95), Oct. 29-Nov. 3, 1995, 1 page.

Totsuka et al., "Frequency Domain Volume Rendering," Sony Corporation, Applicants' Admitted Prior Art, pp. 271-278.

Hylton, Nola M., "Angiographic display method for flow-enhanced MRI", Abstract, Publication Date Jun. 1992, http://adsabs.harvard.edu/abs/1992SPIE.1652.107H, 2 pages.

First Office Action, Chinese Patent Application No. 200680036611.5, Aug. 20, 2010, 27 pages.

* cited by examiner

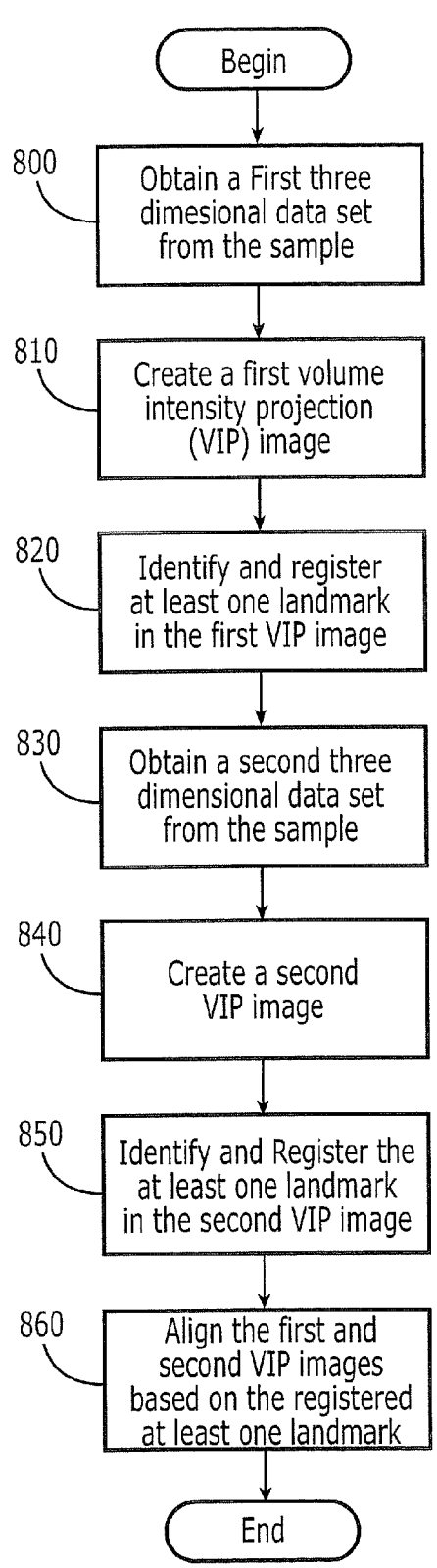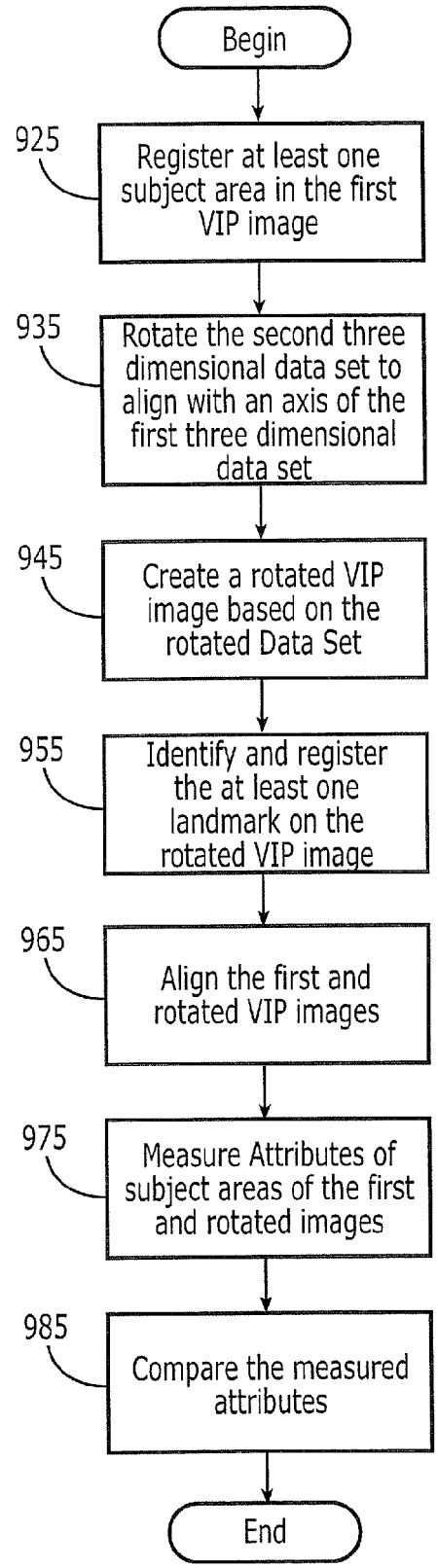
FIGURE 8
FIGURE 9

METHODS, SYSTEMS AND COMPUTER PROGRAM PRODUCTS FOR ANALYZING THREE DIMENSIONAL DATA SETS OBTAINED FROM A SAMPLE

CLAIM OF PRIORITY

The present application claims priority from U.S. Provisional Application No. 60/704,343, filed Aug. 1, 2005, the disclosure of which is hereby incorporated herein by reference as if set forth in its entirety.

FIELD OF THE INVENTION

The present invention relates to imaging systems and, more particularly, to optical coherence imaging systems.

BACKGROUND OF THE INVENTION

Optical Coherence Tomography (OCT) is a technique for imaging into samples, such as tissue, glass and the like. Recent advances in OCT have increased the imaging speed, allowing large image sets, such as three dimensional volumes, to be generated relatively quickly. As OCT is typically high-speed, non-contact and non-destructive, it may be useful for imaging dynamics over short time scales, for example, well below 1.0 second, such as the beating of a heart tube in a fruit fly, and for imaging physiological changes that occur over a long time scales, for example, over days or even longer, such as over the time it takes tissues to develop or to respond to interventions.

A variety of approaches to imaging using OCT are known. Such systems may be characterized as Fourier domain OCT (FD-OCT) and time domain OCT (TD-OCT). FD-OCT generally includes swept source (SS) and spectral domain (SD), where SD systems generally use a broadband source in conjunction with a spectrometer rather than a swept laser source and a photodiode(s). TD systems generally rely on movement of a mirror or reference source over time to control imaging depth by providing coherence depth gating for the photons returning from the sample being imaged. Each system uses broadband optical sources, producing a low effective coherence that dictates the achievable resolution in the depth, or axial, direction.

These imaging techniques are derived from the general field of Optical Low Coherence Reflectometry (OLCR); the time domain techniques are derived from Optical Coherence Domain Reflectometry, swept source techniques are derived from Optical Frequency Domain Reflectometry, and spectral domain techniques have been referred to as "spectral radar."

In contrast to time domain systems, in FD-OCT the imaging depth may be determined by Fourier transform relationships between the acquired spectrum, rather than by the range of a physically scanned mirror, thereby allowing concurrent acquisition of photons from all imaged depths in the sample. Specifically, in FD-OCT, the optical frequency interval between sampled elements of the spectrum may be used to control the imaging depth, with a narrower sampling interval providing a deeper imaging capability.

The use of OCT to make accurate, quantitative measurements over time, may be difficult due to the challenge of ensuring, among other things, that measurements made at different times are taken from the same place in the sample.

With the advent of FD-OCT techniques, it becomes possible to generate practical 3D images, and from these 3D images a planar en-face image. One technique for generating an en-face view and correlating depth-resolved features with landmarks observed on this en-face view are discussed in *Simultaneous acquisition of sectional and fundus ophthalmic images with spectral-domain optical coherence tomography* by Jiao et al. (24 Jan. 2005/Vol. 13, No. 2/OPTICS EXPRESS 445), the content of which is hereby incorporated herein by reference as if set forth in its entirety.

SUMMARY OF THE INVENTION

Some embodiments of the present invention provide methods of analyzing three dimensional data sets obtained from a sample over time. A first three dimensional data set is obtained from the sample at a first time. A first en-face view, or volume intensity projection (VIP) image is created from the first three dimensional data set. One or more first landmarks are identified and registered in the first VIP image. A second three dimensional data set is obtained from the sample at a second time, different from the first time. A second VIP image is created from the second three dimensional data set. The one ore more first landmarks are identified and registered in the second VIP image. The first and second VIP images are aligned based on the registered one or more first landmarks in the first and second VIP images.

In her embodiments of the present invention, one or more subject areas within the three dimensional data set may be registered to the first VIP image. The first and second VIP images may be aligned based on the registered at least one first landmark to locate the registered subject area of the first three dimensional data set in the second three dimensional data set so as to allow comparison of the registered subject area in the first and second three dimensional data sets at the respective first and the second times.

In still further embodiments of the present invention, an attribute of the registered subject area of the first three dimensional data set may be measured and an attribute of the located subject area of the second three dimensional data set may be measured. The measured attributes of the registered and located subject areas may be compared so as to allow comparison of the subject areas at the first and second times. In certain embodiments of the present invention, the first and second three dimensional data sets may be optical coherence tomography (OCT) data sets.

In some embodiments of the present invention, the second three dimensional data set may be rotated to align an axis of the second three dimensional data set with an axis of the first three dimensional data set to obtain a rotated three dimensional data set. A rotated VIP image may be created based on the rotated three dimensional data set.

In further embodiments of the present invention, one or more subject areas may be registered within the first three dimensional data set to the first VIP image. The one or more first landmarks may be registered and identified on the rotated VIP image. The first and rotated VIP images may be aligned based on the registered at least one first landmark in the first and rotated VIP images. The first and rotated VIP images may be aligned based on the registered at least one first landmark to locate the registered subject area of the first three dimensional data set in the rotated three dimensional data set so as to allow comparison of the registered subject area and the located subject area of the first and rotated images, respectively.

In still further embodiments of the present invention, an attribute of the registered subject area of the first three dimensional data set may be measured and an attribute of the located subject area of the rotated three dimensional data set may be measured. The measured attributes of the registered and located common subject areas may be compared so as to allow comparison of the subject areas in the first and rotated three dimensional data sets.

Some embodiments of the present invention provide methods for analyzing three dimensional data sets obtained from a sample, including obtaining a first three dimensional data set from the sample at a first time. A first volume intensity projection (VIP) image is created from the first three dimensional data set. A second three dimensional data set is obtained from the sample at a second time, different from the first time. The second three dimensional data set is rotated to align an axis of the second three dimensional data set with an axis of the first three dimensional data set to obtain a rotated three dimensional data set. A rotated VIP image is created based on the rotated three dimensional data set.

In further embodiments of the present invention, one or more first landmarks may be identified and registered in the first VIP image. One or more subject areas in the first three dimensional data set may be registered to the first VIP image. One or more of the first landmarks may be identified and registered on the rotated VIP image. The first and rotated VIP images may be aligned based on the registered one or more first landmarks in the first and rotated VIP images. The first and rotated VIP images may be aligned based on the registered at least one first landmark to locate the registered subject area in the first three dimensional data set in the rotated three dimensional data set so as to allow comparison of the registered and located subject areas at the first and second times.

In still farther embodiments of the present invention, an attribute of the registered subject area of the first three dimensional data set may be measured and an attribute of the located subject area of the rotated three dimensional data set may be measured. The measured attributes of the registered and located subject areas are compared so as to allow comparison of the subject areas in the first and rotated three dimensional data sets. In certain embodiments of the present invention, the first, second and rotated three dimensional data sets are optical coherence tomography (OCT) data sets.

Some embodiments of the present invention provide methods of analyzing data sets obtained from a sample over time, including identifying and registering one or more landmarks in first and second volume intensity projection (VIP) images created from first and second three dimensional data sets, respectively. The first and second VIP images may be aligned based on the registered at least one first landmark to locate a common subject area in the first and second three dimensional data sets so as to allow comparison of the common subject area in the first and second three dimensional data sets at the first and the second times, respectively.

Although embodiments of the present invention are discussed primarily above with respect to method embodiments, system and computer program product embodiments are also provided herein.

BRIEF DESCRIPTION OF THE DRAWINGS

FIGS. 8 through 13 are flowcharts illustrating operations for analyzing three dimensional data sets obtained from a sample according to various embodiments of the present invention.

DETAILED DESCRIPTION OF THE INVENTION

Figure 1:
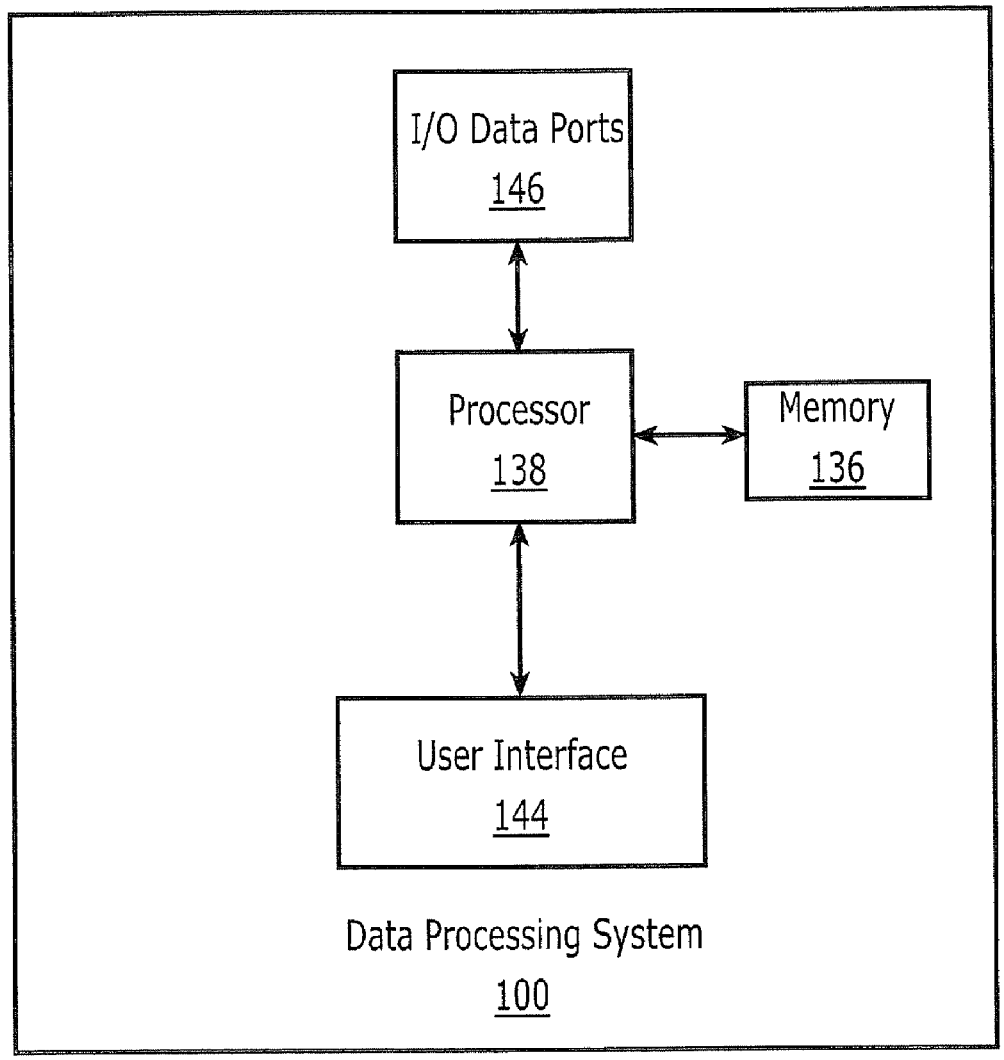
FIG. 1 is a block diagram of a data processing system according to some embodiments of the present invention.

The present invention now will be described more fully hereinafter with reference to the accompanying figures, in which embodiments of the invention are shown. This invention may, however, be embodied in many alternate forms and should not be construed as limited to the embodiments set forth herein. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

It will be understood that, although the terms first, second, etc. may be used herein to describe various elements, these elements should not be limited by these terms. These terms are only used to distinguish one element, from another element. Thus, a first element discussed below could be termed a second element without departing from the teachings of the present invention.

The present invention may be embodied as methods, systems and/or computer program products. Accordingly, the present invention may be embodied in hardware and/or in software (including firmware, resident software, micro-code, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

The present invention is described below with reference to block diagrams and/or flowchart illustrations of devices, methods and computer program products according to embodiments of the invention. It is to be understood that the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

Some embodiments of the present invention will now be discussed with respect to FIGS. 1 through 11. As discussed herein, some embodiments of the present invention provide methods, systems and computer program products that use surface projection images, referred to herein as volume intensity projection (VIP) images, generated from optical coherence tomography (OCT) data to align multiple data sets of a sample taken at different times. It will be understood that VIP images according to some embodiments of the present invention may also be termed summed voxel projections, Fundus images, and the like without departing from the scope of the present invention. Using methods, systems and computer program products according to some embodiments of the present invention, may increase the likelihood or possibly ensure that measurements of a sample taken at different times are taken from the same or substantially the same location in the sample. Various embodiments of the present invention are discussed below including hardware and/or software for an OCT system that provides the capability to generate VIP images from OCT datasets, align datasets taken at different times and/or rotate the images to obtain a different view.

OCT imaging systems may be categorized in two general categories, time domain OCT (TD-OCT), where a moving mirror or prism in the reference arm determines the current imaging depth location in the sample, and Fourier domain OCT (FD-OCT), where there reference arm is fixed in length and data is acquired over a spectrum of wavelengths to change imaging depth location in the sample. FD-OCT is typically further categorized into two categories, swept source OCT (SS-OCT) and spectral domain OCT (SD-OCT). For SS-OCT, a narrow-linewidth laser is typically swept in wavelength over time to interrogate the sample at different wavelengths. For SD-OCT, a broad band (low coherence) source, such as a superluminscent diode (SLD), is typically used in conjunction with a spectrometer. It will be understood that any of these or other functionally similar hardware implementations may be used to generate the data used to generate the VIP images without departing from the scope of the present invention.

It will also be understood that although some embodiments of the present invention are discussed herein with respect to data sets generated using OCT imaging systems, any three dimensional data set may be used without departing from the scope of the present invention. For example, ultrasound data and/or magnetic resonance imaging (MRI) data may be used in some embodiments.

OCT systems typically operate by acquiring depth data at a particular lateral position on the sample, which may be called an A-scan. The OCT beam is moved relative to the sample by any of the various depth adjustment approaches described above and another set of depth data is acquired. These series of depth images may be combined to form a 2-D image, which may be called a B-scan. Any scan pattern can generally be used without departing from the scope of the present invention. For example, commonly used scan patterns include linear and circular scan patterns. By scanning in two directions instead of just one, a three dimensional volume of data can be acquired. Again any scan pattern can generally be used to create the three dimensional image, for example, commonly used three dimensional scan patterns include rectangular, sets of radial lines, and sets of concentric circles.

OCT data is a measurement of the backscattered reflectivity at each depth in the sample at a given point. In other words, the contrast in the image is generally due to variations in the backscattered reflectivity in the sample. A desirable image set that may be extracted is a surface projection of the subsurface scattering data. One way of generating this type of image is by summing the OCT data over an A-scan. This value is the total reflectivity at that particular lateral position. By applying this over a volume scan, a 2-D image may be created. This type of image may be referred to as a Fundus image when generated from OCT data sets of retina scans. Generally, this type of image may be referred to as a VIP image. In some embodiments of the present invention, this image may be, essentially, a black and white picture of the sample.

Various exemplary embodiments of the present invention will be described herein with reference to alignment based on VIP images. As the VIP images are created from the OCT data, there is a direct correlation between pixels on the VIP image and A-scans in the OCT data set. Other algorithms to generate a useful VIP-like image may be used with some embodiments of the present invention as well, such as by summing over a limited subset of an A-scan, and/or by weighting the sum over the A-scan with some selected function suited to a particular use of the scan information.

The VIP image can be used to align the OCT system with respect to the sample in some embodiments when the VIP image is generated in nearly real time. The alignment VIP image may be acquired at a lower lateral resolution, which may increase the rate at which the VIP images are created. This image may allow the user to align the system based on OCT data, thus providing a preview of the OCT dataset. This approach in some embodiments may be more accurate than trying to visually align the sample to the OCT system or using a video camera for alignment.

As multiple OCT data sets are taken and VIP images are generated from the datasets, according to some embodiments of the present invention, the VIP images can be used to align OCT datasets taken at different times and possibly ensure that subject pathologies (targets) observed within various datasets taken at different times are from the same location in the sample. In order to align the images, one or more landmarks in the sample may be identified and used. As used herein, "landmarks" refer to elements of the sample, the locations of which do not significantly change over time, for example, a branch point of a retinal blood vessel in an eye sample may be a landmark. Since the locations of the landmarks do not significantly change over time, the location(s) of targets may be referenced with respect to the landmarks and, therefore, these same or similar location(s) can be located in the future.

For example, in OCT datasets from retinas (eye samples), the VIP, or Fundus, image typically clearly shows the location of blood vessels, the optic nerve head, and the fovea. Using the blood vessels and/or optic nerve head as landmarks according to some embodiments of the present invention, two or more retinal images taken from the same person at different times can be aligned by aligning the landmarks. The degrees of freedom for alignment of the samples may include, for example, translational in X & Y, rotational in theta, and/or scaling in X & Y.

As used herein, the VIP plane is orthogonal to the individual A-scans. However, in some embodiments, any other plane may be defined by a three-degree-of-freedom rotation about the scan axis. This plane may then become a reference plane for landmark identification, and subsequent images may be aligned with an original image applying these three additional degrees of freedom.

Once aligned, one or more measurements can be made, generally in a direction orthogonal to the reference Fundus plane, on one or more datasets at the same location in each dataset for a particular measurement. These measurements can include almost any value of interest, relative scattering strength, such as layer thickness, the distance between two points, the volume of a cavity or feature, and time-rate-of-change measurements, and/or Doppler flow measurements. By measuring the location of one or more particular points relative to one or more landmarks over time, velocities and accelerations can be calculated from the change in position over known time interval(s) and the change in velocity over known time interval(s).

Although retinal OCT is discussed herein as an example for explaining some embodiments of the present invention, it will be understood that some embodiments of the present invention may operate for any three dimensional datasets, including OCT datasets, such as, those from an OCT microscope and OCT systems for endoscopic applications. In some embodiments of the present invention, the landmarks in the sample can either be part of the sample, such as blood vessels in the retina and/or artificially introduced landmarks, such as holes drilled into a MEMS sample or surgically introduced pellets in a tissue sample or painted landmarks without departing from the scope of the present invention.

In some embodiments of the present invention, the location of the OCT image acquisition may be separated in time and space from the generation of the VIP image and again from the alignment of multiple images and again from the acquisition of measurements of interest from the datasets. For example, a portable OCT imaging system could be used in an animal facility to acquire daily images. The daily images may be transferred over a network to a central server, where once a week all the data is processed and longitudinal measurements of retinal thickness are generated.

In some embodiments of the present invention, the level of automation in the process may vary. In particular embodiments, all the operations described herein for image acquisition may be automated in software, but varying degrees of reduced automation may be provided in some embodiments without departing from the scope of the present invention. For example, in some embodiments, the user may align the multiple VIP images on the computer screen including the X & Y translation, rotation, and/or X & Y scaling. Furthermore, the determination of the measurement of interest may be based on user input and/or may happen automatically in software.

Details of various embodiments of the present invention will be discussed below with respect to FIGS. 1 through 11. Referring first to FIG. 1, an exemplary embodiment of a data processing system 100 suitable for use in accordance with some embodiments of the present invention will be discussed. The data processing system 100 typically includes a user interface 144, such as a keyboard, keypad, touchpad or the like, I/O data ports 146 and a memory 136 that communicate with a processor 138. The I/O data ports 146 can be used to transfer information between the data processing system 100 and another computer system or a network. These components may be conventional components, such as those used in many conventional data processing systems, which may be configured to operate as described herein.

Figure 2:
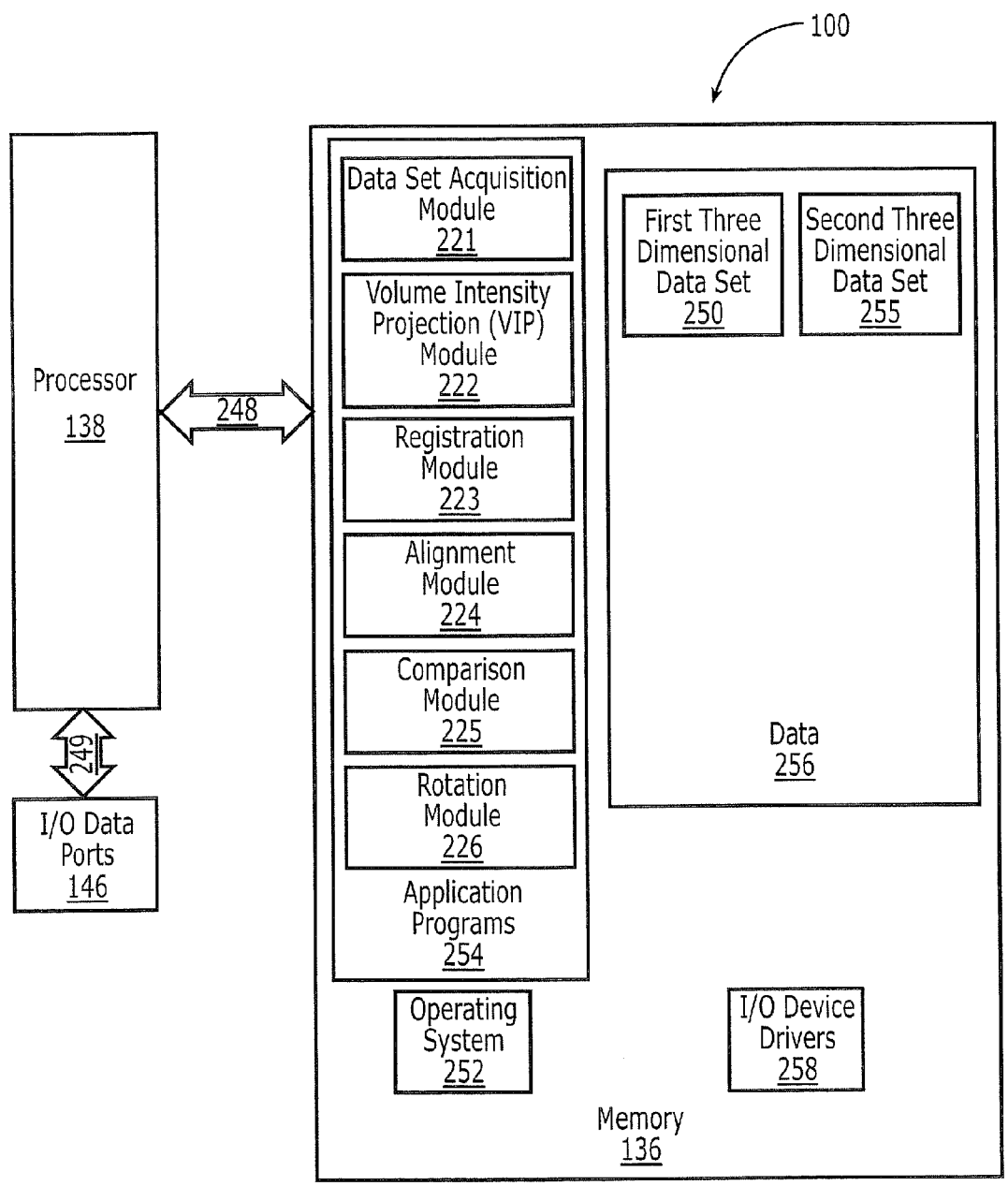
FIG. 2 is a more detailed block diagram of data processing systems according to some embodiments of the present invention.

Referring now to FIG. 2, a more detailed block diagram of the data processing system 100 in accordance with some embodiments of the present invention will be discussed. The processor 138 communicates with the memory 136 via an address/data bus 248 and the I/O data ports 146 via an address/date bus 249. The processor 138 can be any commercially available or custom microprocessor. The memory 136 is representative of the overall hierarchy of memory devices containing the software and data used to implement the functionality of the data processing system 100. The memory 136 can include, but is not limited to, the following types of devices: cache, ROM, PROM, EPROM, EEPROM, flash memory, SRAM, and DRAM.

As shown in FIG. 2, the memory 136 may include several categories of software and data used in the data processing system 100: an operating system 252; application programs 254; input/output (I/O) device drivers 258; and data 256. As will be appreciated by those of skill in the art, the operating system 252 may be any operating system suitable for use with a data processing system, such as OS/2, AIX or zOS from International Business Machines Corporation, Armonk, N.Y., Windows95, Windows98, Windows2000 or WindowsXP from Microsoft Corporation, Redmond, Wash., Unix or Linux. The I/O device drivers 258 typically include software routines accessed through the operating system 252 by the application programs 254 to communicate with devices such as the I/O data port(s) 146 and certain memory 136 components. The application programs 254 are illustrative of the programs that implement the various features of the data processing system 100 and preferably include at least one application that supports operations according to some embodiments of the present invention. Finally, the data 256 represents the static and dynamic data used by the application programs 254, the operating system 252, the I/O device drivers 258, and other software programs that may reside in the memory 136.

As illustrated in FIG. 2, the data 256 according to some embodiments of the present invention may include three dimensional data sets 250 and 255 obtained from a sample, for example, an eye. Although the data 256 only includes two sets of data sets 250 and 255, embodiments of the present invention are not limited to this configuration. One data set or more than two data sets may be present without departing from the scope of the present invention.

As further illustrated in FIG. 2, the application programs 254 may include a data set acquisition module 221, a volume intensity projection (VIP) module 222, a registration module 223, an alignment module 224, a comparison module 225 and a rotation module 226 according to some embodiments of the present invention. While the present invention is illustrated, for example, with reference to the data set acquisition module 221, the VIP module 222, the registration module 223, the alignment module 224, the comparison module 225 and the rotation module 226 being application programs in FIG. 2, as will be appreciated by those of skill in the art, other configurations may also be utilized while still benefiting from the teachings of the present invention. For example, the data set acquisition module 221, the VIP module 222, the registration module 223, the alignment module 224, the comparison module 225 and the rotation module 226 may also be incorporated into the operating system 252 or other such logical division of the data processing system 100. Thus, the present invention should not be construed as limited to the configuration of FIG. 2, but is intended to encompass any configuration capable of carrying out the operations described herein.

Furthermore, while the data set acquisition module 221, the VIP module 222, the registration module 223, the alignment module 224, the comparison module 225 and the rotation module 226 are illustrated in a single data processing system, as will be appreciated by those of skill in the art, such functionality may be distributed across one or more data processing systems. Thus, the present invention should not be construed as limited to the configuration illustrated in FIGS. 1 through 2, but may be provided by other arrangements and/or divisions of function between data processing systems.

In particular, the data set acquisition module 221 is configured to obtain three dimensional data sets from a sample. The three dimensional data sets can be any type of three dimensional data, for example, sonogram data, MRI data and/or OCT data. The data sets may be obtained from the sample at different times. Having data sets of the sample, for example, the human eye, taken at different times may allow comparison of the sample to determine if anything in the sample has changed over time. For example, a first three dimensional data set may be obtained from the sample at a first time and a second three dimensional data set may be obtained from the sample at a second time, different from the first time.

Once one or more data sets are obtained, the volume intensity projection (VIP) module 222 may be configured to create a VIP image from the three dimensional data set. For example, a first VIP image may be created from the first three dimensional data set and a second VIP image may be created from the second three dimensional data set.

To allow the first and second VIP images to be compared, the registration module 223 may be configured to identify and register one or more landmarks in the VIP image(s). As discussed above, landmarks refer to elements of the sample, the locations of which do not significantly change over time, for example, a branch point of a retinal blood vessel in an eye sample may be a landmark. Since the location of the landmarks do not significantly change over time, the location(s) of samples may be referenced with respect to the landmarks and, therefore, these same or similar location(s) can be located in the future as will be discussed further below.

In some embodiments of the present invention, the registration module 223 may be further configured to register one or more subject areas in the first VIP image. As used herein, a "subject area" refers to any area of interest in the sample, for example, an area of the sample that includes cancer cells. This subject area may be located in the VIP images taken at various times by the subject areas relation to the registered landmarks on the VIP images.

The alignment module 224 may be configured to align the first and second VIP images based on the registered one or more landmarks in the VIP image(s) as will be discussed further below with respect to FIG. 5. In particular, an alignment module configured to align the first and second VIP images based on the registered one or more landmarks in the first and second VIP images. The alignment module 224 may be further configured to align the first and second VIP images based on the registered one or more landmarks to locate the registered subject area of the first three dimensional data set in the second three dimensional data set so as to allow comparison of the registered subject area in the first and second three dimensional data sets at the respective first and the second times. Thus, according to some embodiments of the present invention, a change in the subject area of the sample may be monitored over time so as to allow a determination of whether the condition being monitored is the same, better or worse.

The comparison module 225 may be configured to measure an attribute of the registered subject area of the first three dimensional data set. As used herein, an attribute of the subject area can be any aspect of the subject area that may be of interest. For example, an attribute of the subject area may be the size of the area affected by cancer. The comparison module 225 may be further configured to measure an attribute of the subject area located in the second three dimensional data set based on the registered subject area in the first three dimensional data set. In some embodiments of the present invention, the comparison module 225 may be configured to compare the measured attributes of the registered and located subject areas so as to allow comparison of the subject areas at the first and second times. Thus, according to some embodiments of the present invention, three dimensional data sets created at different times containing the subject area of the sample may be compared. This comparison may be used to, for example, determine if the monitored condition is the same, worse or better.

In some embodiments of the present invention, the rotation module 226 may be configured rotate a three dimensional data set to align an axis of the three dimensional data set with an axis of the second three dimensional data set. For example, an axis of the first three dimensional data set may be rotated to align an axis of the first three dimensional data set with an axis of the second three dimensional data set to obtain a rotated three dimensional data set. In these embodiments of the present invention, the VIP module 222 may be farther configured to create a rotated VIP image based on the rotated three dimensional data set.

In some embodiments of the present invention, the registration module 223 may be further configured to register one or more subject areas in the first VIP image and identify and register the one or more landmarks on the rotated VIP image. The alignment module 224 may be further configured to align the first and rotated VIP images based on the registered one or more landmarks in the first and rotated VIP image and align the first and rotated VIP images based on the registered one or more landmarks to locate the registered subject area in the first three dimensional data set in the rotated three dimensional data set so as to allow comparison of the registered subject area and the located subject area of the first and rotated three dimensional data set, respectively.

Exemplary embodiments of the present invention will now be discussed with respect to a Fundus image, a Fundus image being a VIP originating from an OCT image of a retina. Although embodiments of the present invention are discussed herein with respect to Fundus images, embodiments of the present invention are not limited to this configuration. For example, any VIP image could be used without departing from the scope of the present invention.

Figure 3:
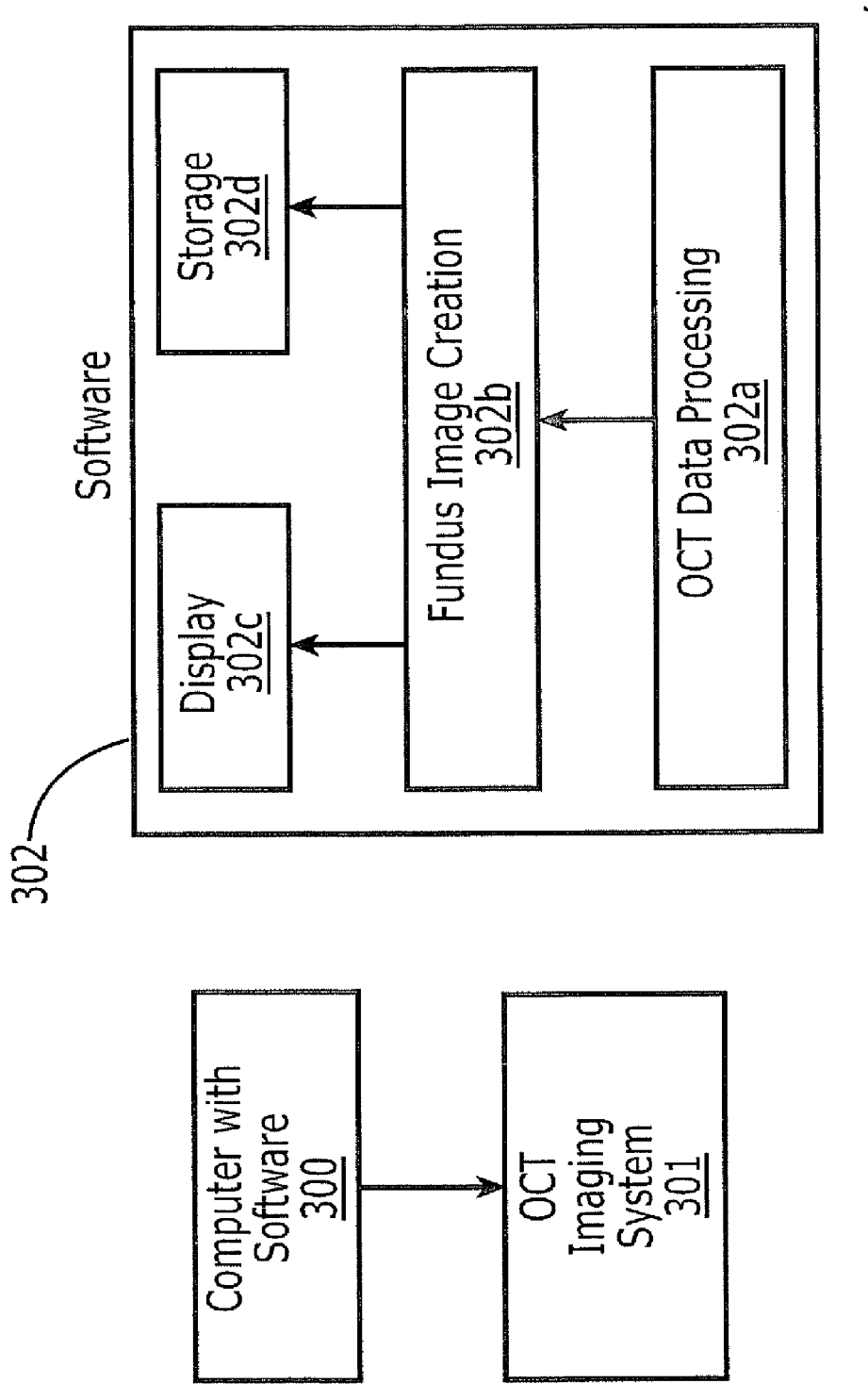
FIG. 3 is a schematic block diagram illustrating an optical coherence tomography (OCT) system according to some embodiments of the present invention.

Referring now to FIG. 3, a schematic block diagram illustrating an OCT system according to some embodiments of the present invention will be discussed. As illustrated in FIG. 1, the OCT system includes a computer running software 300 and an OCT imaging system 301. FIG. 1 also illustrates the components of the software (memory) 302 running on the computer 300. As illustrated, the computer 300 is connected to the OCT imaging system 301. The computer executes software that may be resident in memory 302. Various software modules in the memory 302 may, among other things, process raw data to create OCT image datasets, for example, A-scans, B-scans and/or volume images 302a, generate Fundus or VIP images from the OCT datasets 302b, display data to a user display, for example, a monitor, or the like 302c, and/or store data 302d.

Figure 4:
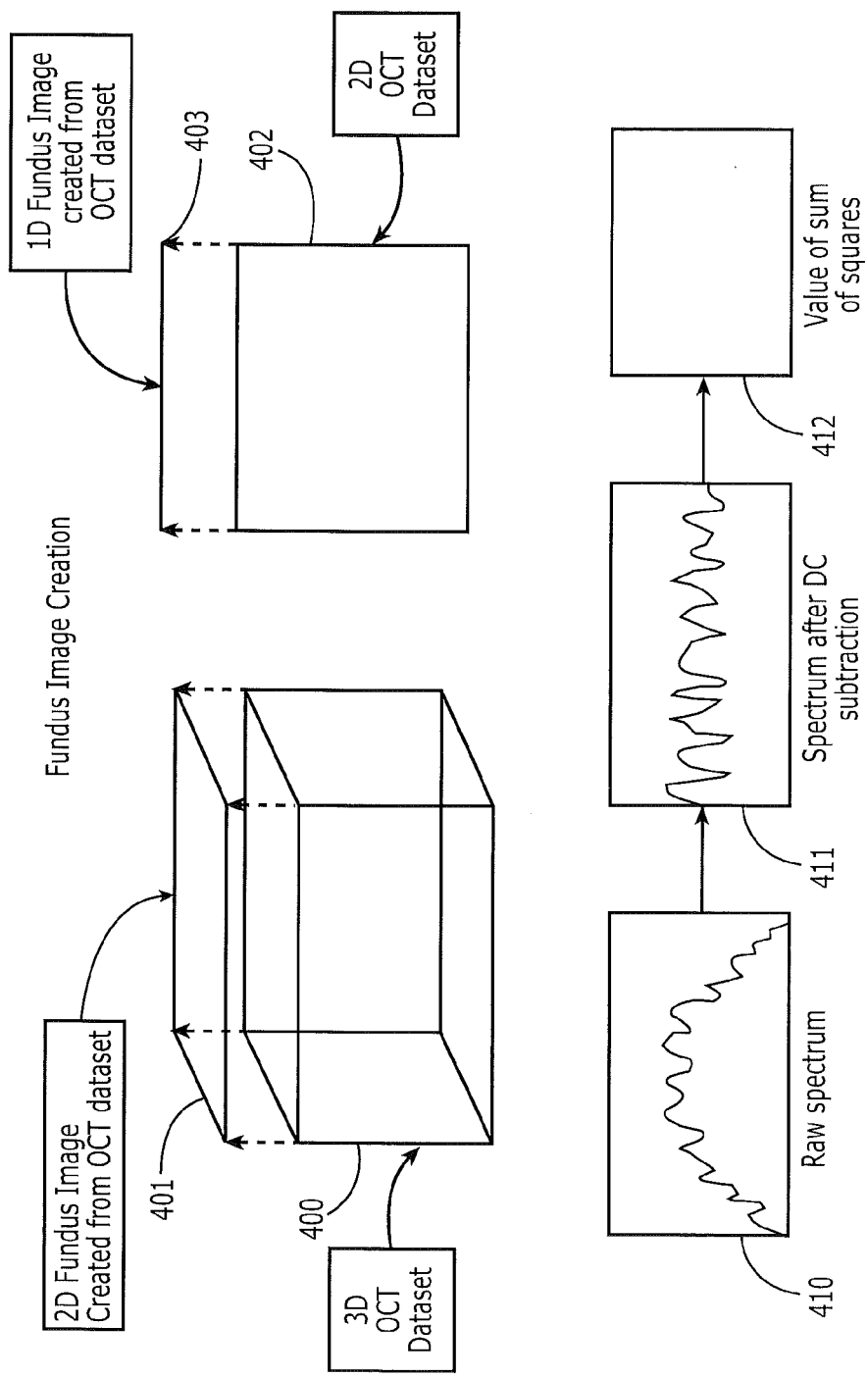
FIG. 4 is a schematic diagram that illustrates creation of a Fundus image according to some embodiments of the present invention.

Referring now to FIG. 4, a schematic diagram illustrating creation of a Fundus image according to some embodiments of the present invention will be discussed. As illustrated in FIG. 4, the OCT dataset 400 may be converted into a Fundus image 401 by taking the raw spectral data 410, subtracting the DC spectrum to provide the spectrum after substracting the DC spectrum 411, and squaring and slumming the remaining spectrum to arrive at a number that is the measure of total reflectivity 412. This is repeated for the A-scans in the three dimensional dataset to generate a 2D image (the Fundus image) 401. The same procedure can be used to generate a 1D line image 403 from a 2D B-scan 402.

Figure 5:
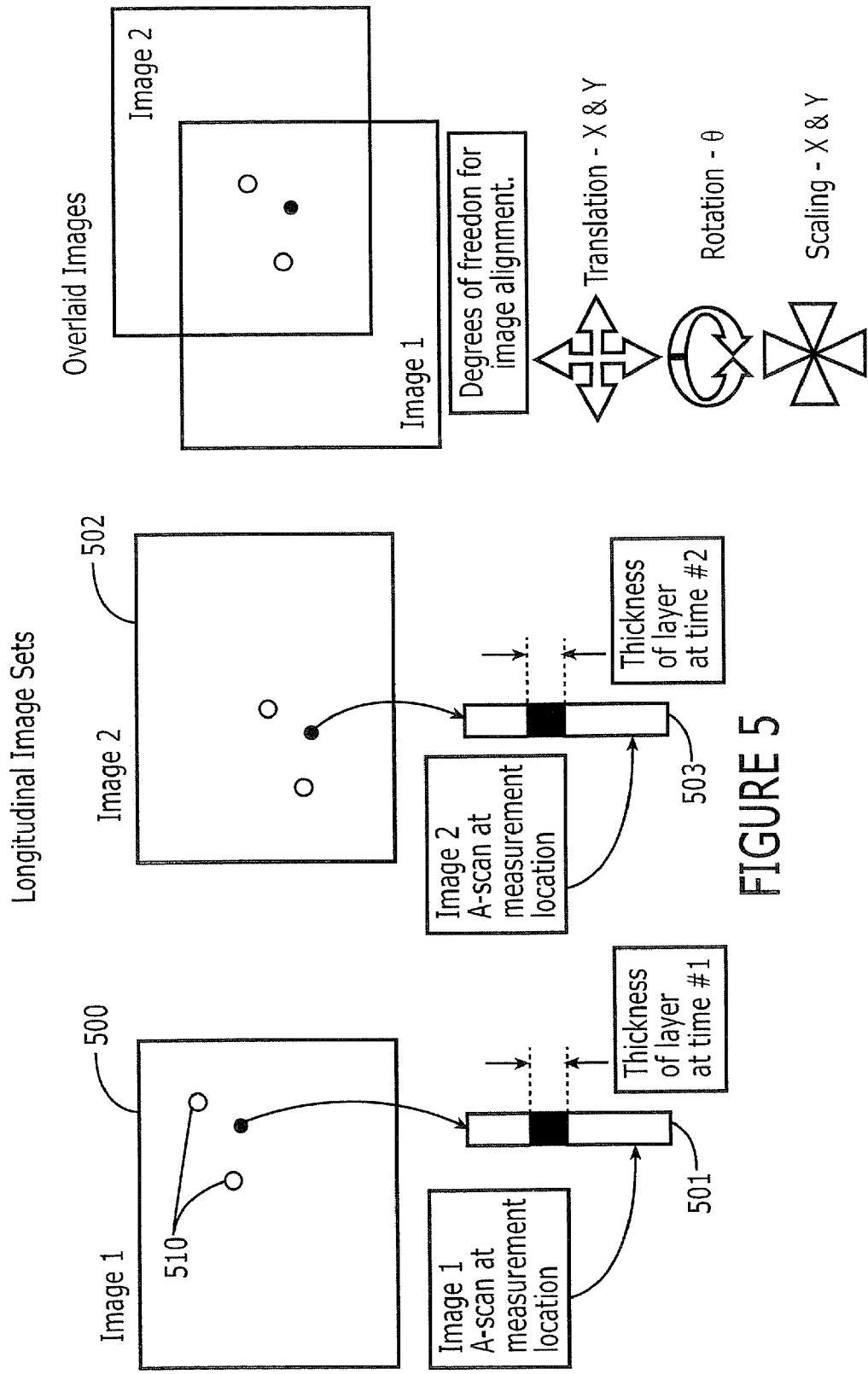
FIG. 5 is a schematic diagram illustrating alignment of two images according to some embodiments of the present invention.

Referring now to FIG. 5, a schematic diagram illustrating alignment of two images according to some embodiments of the present invention will be discussed. As illustrated in FIG. 5, once the Fundus images are generated, multiple OCT datasets can be aligned using landmarks 510 on the Fundus image. In particular, a measurement is taken in the Fundus image 1 500 from a particular A-scan 501 at a point relative to two landmarks. A second OCT dataset is acquired at a later time and a Fundus image 2 502 is generated from that dataset. By aligning the two Fundus images 500 and 502, the same measurement location can be determined and the second A-scan 503 from the same location can be selected. This may work for any number of OCT datasets and Fundus images. Also, the number of landmarks 510 can vary and the measurement to be acquired can be almost anything in various embodiments, including thickness measurements, distance measurements, volume measurements, Doppler flow measurements, and/or other measurements.

Figure 6:
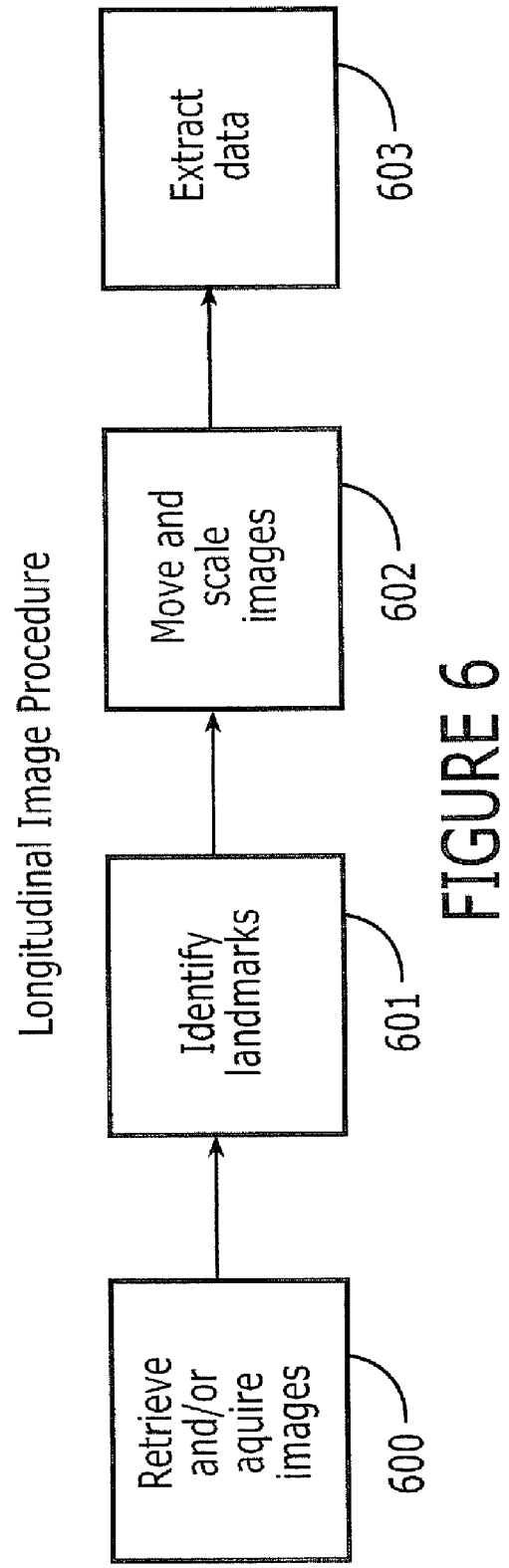
FIG. 6 is a flowchart illustrating methods for aligning two or more images according to some embodiments of the present invention.

Referring now to FIG. 6, a flowchart illustrating methods for aligning two or more images according to some embodiments of the present invention will be discussed. As illustrated in FIG. 6, operations begin with retrieving and/or acquiring OCT image datasets (block 600). Fundus images may be generated at block 600. Landmarks are identified, for example, as described above using Fundus images (block 601). The images are moved and scaled to provide alignment based on the identified landmarks (block 602). Data is extracted from the aligned images (block 603).

Figure 7:
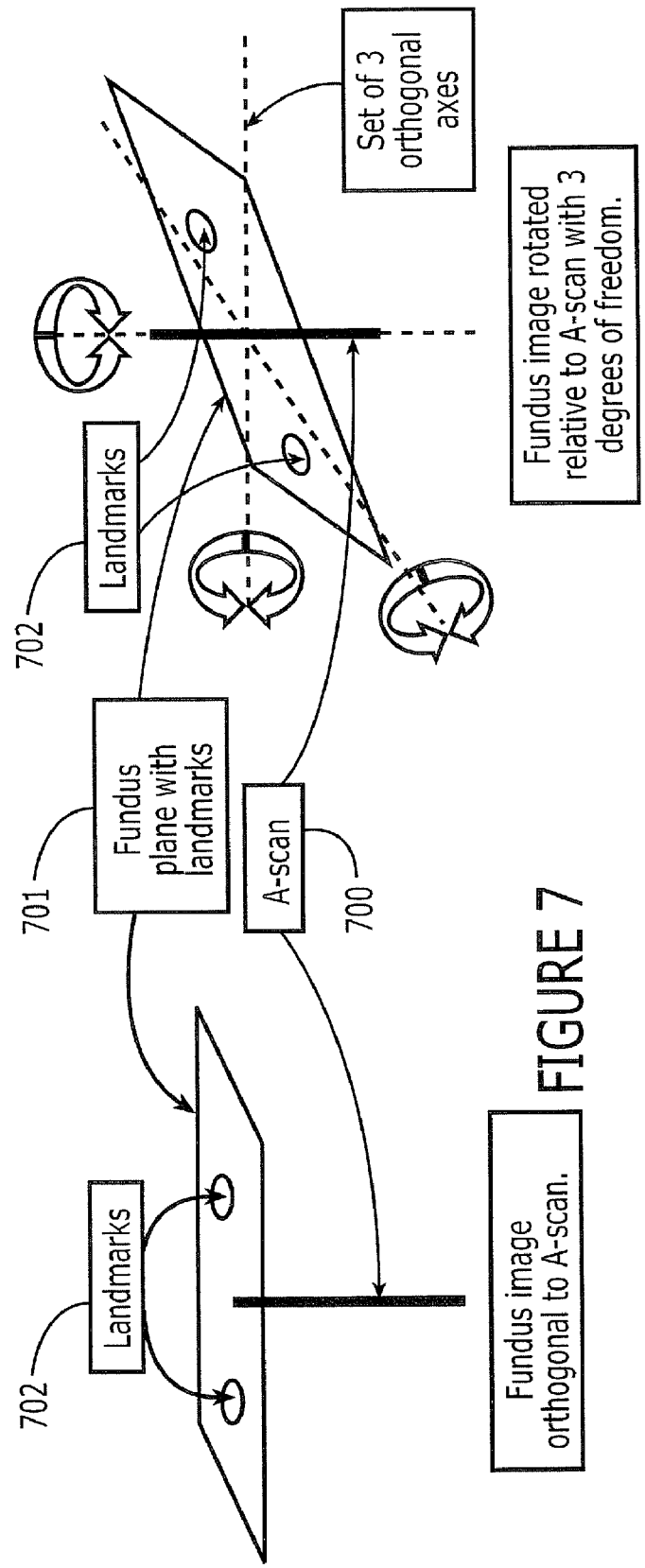
FIG. 7 is a schematic diagram illustrating Fundus images orthogonal to A-scan and rotated relative to A-scan according to some embodiments of the present invention.

Referring now to FIG. 7, a schematic diagram illustrating Fundus images orthogonal to A-scan and rotated relative to A-scan according to some embodiments of the present invention will be discussed. The embodiments illustrated in FIG. 7 may, in some respects, correspond to those described with reference to FIG. 4. However, in the embodiments of FIG. 7, the Fundus image plane 701 is rotated in 1, 2 and/or 3 axis relative to the A-scan 700. The Fundus image plane 701 is illustrated with as containing landmarks 702 for reference and alignment of multiple OCT datasets and the procedure for longitudinal data extraction may remain generally the same.

Operations according to some embodiments of the present invention will now be discussed with respect to the flowcharts of FIGS. 8 through 13. Referring first to FIG. 8, operations for analyzing three dimensional data sets obtained from a sample over time will be discussed. Operations begin at block 800 by obtaining a first three dimensional data set from the sample at a first time. The three dimensional data set may be any three dimensional data set without departing from the scope of the present invention. For example, the three dimensional data set may be sonogram data, MM data and/or OCT data. A first VIP image is created from the first three dimensional data set (block 810). One or more first landmarks may be registered on the first VIP image (block 820). Landmarks refer to elements of the sample, the locations of which do not significantly change over time, for example, a retina in an eye sample may be a landmark. A second three dimensional data set is obtained from the sample at a second time, different from the first time (block 830). A second VIP image is created from the second three dimensional data set (block 840). The one or more landmarks are identified and registered in the second VIP image (block 850). The first and second VIP images may be aligned based on the registered one or more landmarks in the first and second VIP images as discussed above with respect to FIG. 5 (block 860).

Operations according to further embodiments of the present invention will now be discussed with respect to the flowchart of FIG. 9. As illustrated therein, one or more subject areas may be registered in the first VIP image (block 925). As discussed above, a subject area is any area of interest in the sample. The second three dimensional data set may be rotated to align an axis of the second three dimensional data set with an axis of the first three dimensional data set to obtain a rotated three dimensional data set (block 935). A rotated VIP image may be created based on the rotated three dimensional data set (block 945). The one or more first landmarks may be identified and registered in the rotated VIP image (block 955).

The first and rotated VIP images may be aligned based on the registered one or more first landmarks in the first and rotated VIP images (block 965). In some embodiments of the present invention, alignment may include aligning the first and rotated VIP images based on the registered one or more first landmarks to locate the registered subject area in the first three dimensional data set in the rotated three dimensional data set so as to allow comparison of the registered subject area and the located subject area of the first and rotated three dimensional data set, respectively.

An attribute of the registered subject area of the first three dimensional data set may be measured and an attribute of the located subject area of the rotated three dimensional data set may be measured (block 975). The measured attributes of the registered and located common subject areas may be compared so as to allow comparison of the subject areas in the first and rotated three dimensional data set (block 985).

Figure 10:
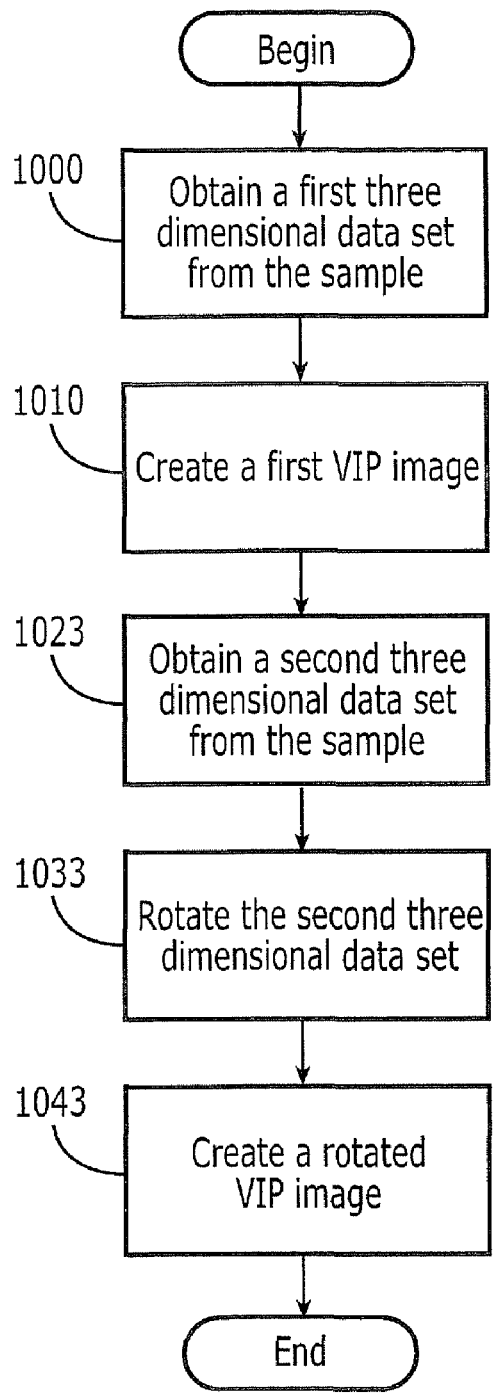

Operations for analyzing three dimensional data sets obtained from a sample according to further embodiments of the present invention will now be discussed with respect to the flowchart of FIG. 10. Operations begin at block 1000 by obtaining a first three dimensional data set from the sample at a first time. A first volume intensity projection (VIP) image is created from the first three dimensional data set (block 1010). A second three dimensional data set is obtained from the sample at a second time, different from the first time (block 1023). The second three dimensional data set is rotated to align an axis of the second three dimensional data set with an axis of the first three dimensional data set to obtain a rotated three dimensional data set (block 1033). A rotated VIP image is created based on the rotated three dimensional data set (block 1043).

Figure 11:
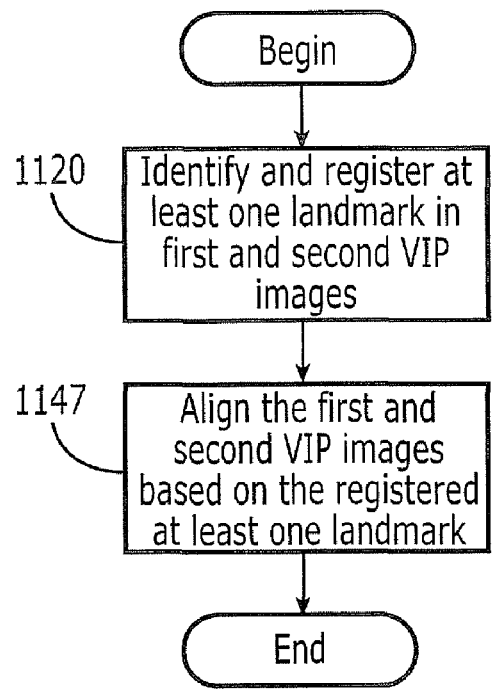

Operations for analyzing data sets obtained from a sample over time according to further embodiments of the present invention will now be discussed with respect to the flowchart of FIG. 11. Operations begin at block 1120 by identifying and registering one or more landmarks in first and second VIP images created from first and second three dimensional data sets, respectively. The first and second VIP images are aligned based on the registered at least one first landmark to locate a common subject area in the first and second three dimensional data sets so as to allow comparison of the common subject area in the first and second three dimensional data sets at the first and the second times, respectively (block 1147).

Figure 12:
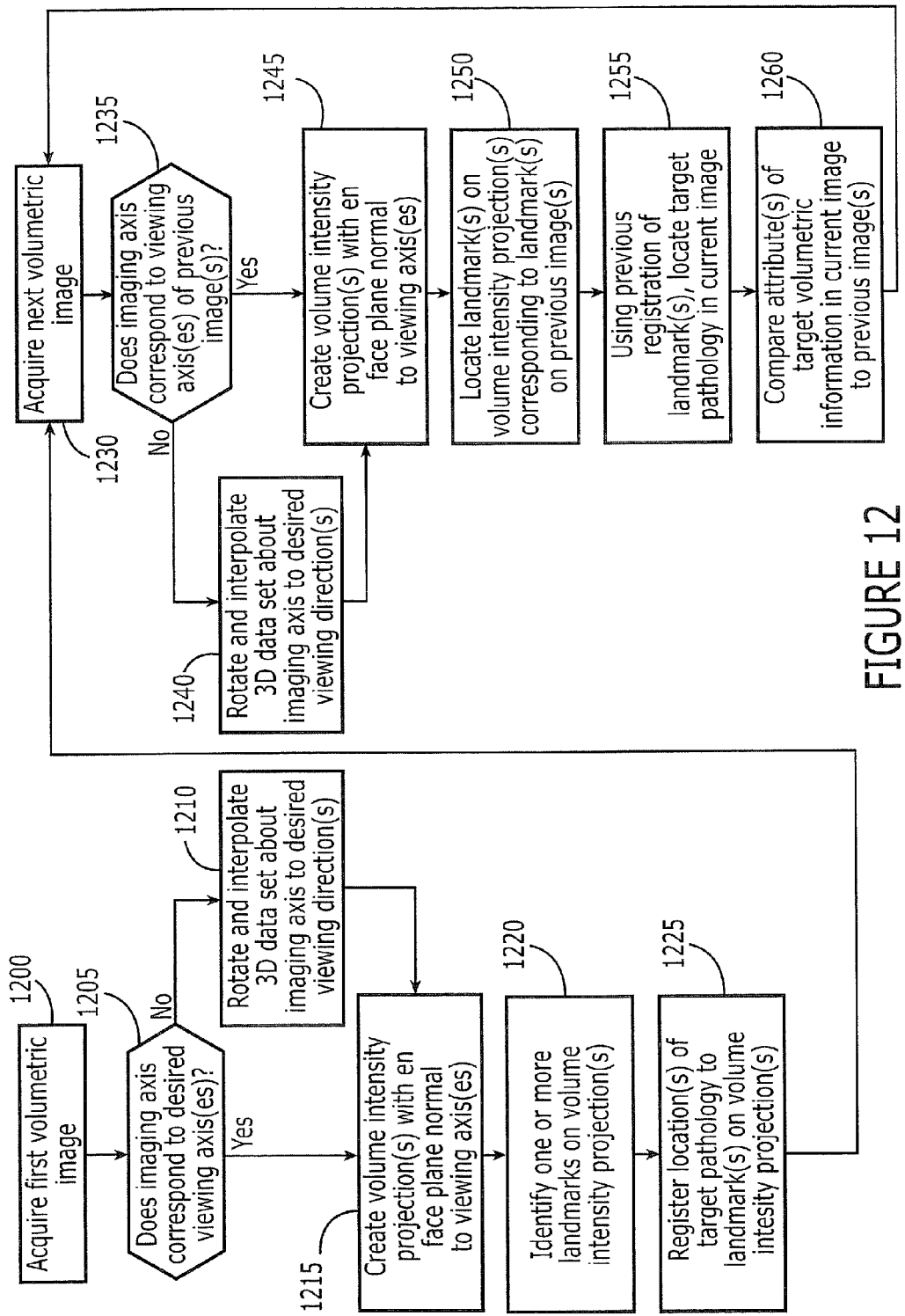

Operations for analyzing data sets obtained from a sample over time according to further embodiments of the present invention will now be discussed with respect to the flowchart of FIG. 12. Operations begin at block 1200 by acquiring a first volumetric image from a first three dimensional data set. It is determined if the volumetric image corresponds to a desired viewing axis (block 1205). If it is determined that the volumetric image does not correspond to a desired viewing axis (block 1205), the three dimensional data set is rotated and interpolated about the imaging axis until the desired viewing axis is obtained (block 1210) and operations proceed to block 1215 discussed below.

If, on the other hand it is determined that the volumetric image does correspond to the desired viewing axis (block 1205), a VIP image is created having an en face plane that is normal to the viewing axis (block 1215). One or more landmarks may be identified on the VIP image (block 1220). The locations of one or more subject areas (target pathologies) may be registered to the one or more landmarks on the VIP image (block 1225).

A second or next volumetric image is acquired (block 1230). It is determined if the second or next volumetric image corresponds to a desired viewing axis (block 1235). If it is determined that the second or next volumetric image does not correspond to a desired viewing axis (block 1235), the three dimensional data set is rotated and interpolated about the imaging axis until the desired viewing axis is obtained (block 1240) and operations proceed to block 1245 discussed below.

If, on the other hand it is determined that the second or next volumetric image does correspond to the desired viewing axis (block 1235), a second or next VIP image is created having an en face plane that is normal to the viewing axis (block 1245). The one or more landmarks may be identified on the second or next VIP image (block 1250). The locations of one or more subject areas (target pathologies) may be registered to the one or more landmarks on the VIP image (block 1255). Attributes of subject areas of the first and second VIP images may be compared as discussed above (block 1260). Operations of blocks 1230 through 1260 may repeat until all images have been processed.

Figure 13:
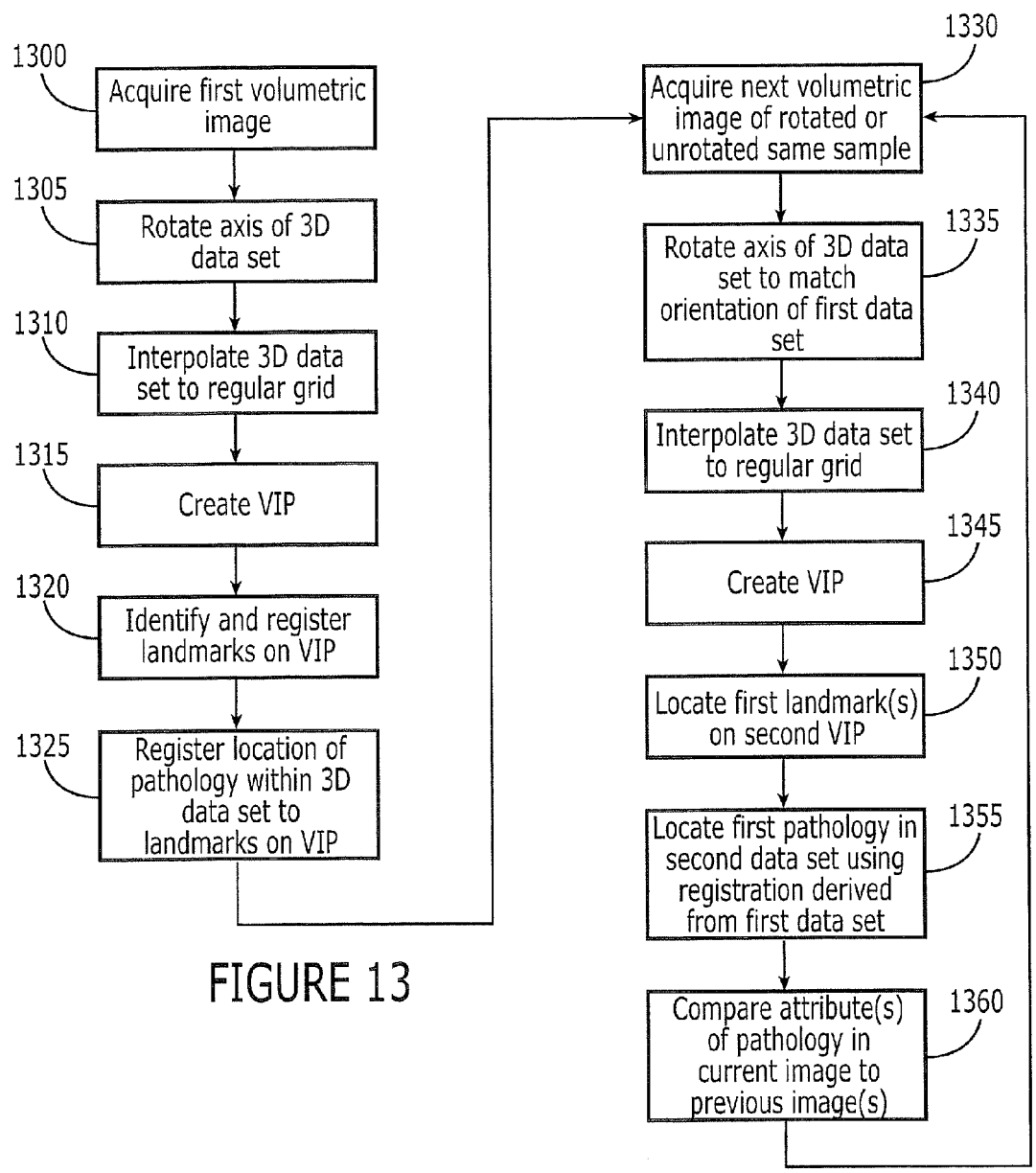

Operations for analyzing data sets obtained from a sample over time according to further embodiments of the present invention will now be discussed with respect to the flowchart of FIG. 13. Operations begin at block 1300 by acquiring a first volumetric image from a first three dimensional data set. The axis of the three dimensional data set may be rotated (block 1305) and interpolated to a regular grid (block 1310). A first VIP image is created (block 1315). One or more landmarks may be identified and registered on the first VIP image (block 1320). The locations of one or more subject areas (target pathologies) may be registered to the one or more landmarks on the first VIP image (block 1325).

A second or next volumetric image is acquired (block 1330). The axis of the second or next three dimensional data set may be rotated to match the orientation of the first VIP image (block 1335). The three dimensional data of the second or next volumetric image may be interpolated to a regular grid (block 1340). A second or next VIP image is created (block 1345). The one or more landmarks may be identified and registered on the second or next VIP image (block 1350). The locations of one or more subject areas (target pathologies) may be located in the second or next VIP image based on the registered subject area in the first VIP image (block 1355). Attributes of subject areas of the first and second VIP images may be compared as discussed above (block 1360). Operations of blocks 1330 through 1360 may repeat until all images have been processed.

In the drawings and specification, there have been disclosed embodiments of the invention and, although specific terms are employed, they are used in a generic and descriptive sense only and not for purposes of limitation, the scope of the invention being set forth in the following claims.

That which is claimed is:

1. A method of analyzing three dimensional data sets obtained from a sample over time, comprising:
    obtaining a first three dimensional data set from the sample at a first time;
    creating a first volume intensity projection (VIP) image from the first three dimensional data set;
    identifying and registering at least one first landmark in the first VIP image;
    obtaining a second three dimensional data set from the sample at a second time, different from the first time;
    creating a second VIP image from the second three dimensional data set;
    identifying and registering the at least one first landmark in the second VIP image; and
    aligning the first and second VIP images based on the registered at least one first landmark in the first and second VIP images.

2. The method of claim 1:
    wherein identifying and registering at least one first landmark in the first VIP image is followed by registering at least one subject area in the first three dimensional data set; and
    wherein aligning further comprises aligning the first and second VIP images based on the registered at least one first landmark to locate the registered subject area of the first three dimensional data set in the second three dimensional data set so as to allow comparison of the registered subject area in the first and second three dimensional data sets at the respective first and the second times.

3. The method of claim 2, further comprising:
    measuring an attribute of the registered subject area of the first VIP image;
    measuring an attribute of the located subject area of the second VIP image; and
    comparing the measured attributes of the registered and located subject areas so as to allow comparison of the subject areas at the first and second times.

4. The method of claim 1, wherein the first and second three dimensional data sets are optical coherence tomography (OCT) data sets.

5. The method of claim 1, further comprising:
    rotating the second three dimensional data set to align an axis of the second three dimensional data set with an axis of the first three dimensional data set to obtain a rotated three dimensional data set; and
    creating a rotated VIP image based on the rotated three dimensional data set.

6. The method of claim 5, wherein identifying and registering at least one first landmark in the first VIP image is followed by registering at least one subject area in the first three dimensional data set, the method further comprising:
    identifying and registering the at least one first landmark on the rotated three dimensional data set; and aligning the first and rotated VIP images based on the registered at least one first landmark in the first and rotated VIP images, wherein aligning includes aligning the first and rotated VIP images based on the registered at least one first landmark to locate the registered subject area in the first three dimensional data set in the rotated three dimensional data set so as to allow comparison of the registered subject area and the located subject area of the first and rotated three dimensional data sets, respectively.

7. The method of claim 6, further comprising:
measuring an attribute of the registered subject area of the first three dimensional data set;
measuring an attribute of the located subject area of the rotated three dimensional data set; and
comparing the measured attributes of the registered and located common subject areas so as to allow comparison of the subject areas in the first and rotated three dimensional data set.

8. A method for analyzing three dimensional data sets obtained from a sample, comprising:
obtaining a first three dimensional data set from the sample at a first time;
creating a first volume intensity projection (VIP) image from the first three dimensional data set;
obtaining a second three dimensional data set from the sample at a second time, different from the first time;
rotating the second three dimensional data set to align an axis of the second three dimensional data set with an axis of the first three dimensional data set to obtain a rotated three dimensional data set; and
creating a rotated VIP image based on the rotated three dimensional data set.

9. The method of claim 8, further comprising:
identifying and registering at least one first landmark in the first VIP image;
registering at least one subject area in the first three dimensional data set;
identifying and registering the at least one first landmark on the rotated VIP image; and
aligning the first and rotated VIP images based on the registered at least one first landmark in the first and rotated VIP images, wherein aligning includes aligning the first and rotated VIP images based on the registered at least one first landmark to locate the registered subject area in the first three dimensional data set in the rotated three dimensional data set so as to allow comparison of the registered and located subject areas at the first and second times.

10. The method of claim 8, further comprising:
measuring an attribute of the registered subject area of the first three dimensional data set;
measuring an attribute of the located subject area of the rotated three dimensional data set; and
comparing the measured attributes of the registered and located subject areas so as to allow comparison of the subject areas in the first and rotated three dimensional data set.

11. The method of claim 8, wherein the first, second and rotated three dimensional data sets are optical coherence tomography (OCT) data sets.

12. A computer program product for analyzing three dimensional data sets obtained from a sample, the computer program product comprising computer program code embodied in a computer readable medium, the computer program code comprising program code configured to carry out the method of claim 8.

13. A computer system configured to carry out the method of claim 8.

14. A method of analyzing data sets obtained from a sample over time, comprising:
identifying and registering at least one landmark in first and second volume intensity projection (VIP) images created from first and second three dimensional data sets, respectively; and
aligning the first and second VIP images based on the registered at least one first landmark to locate a common subject area in the first and second three dimensional data sets so as to allow comparison of the common subject area in the first and second three dimensional data sets at first and the second times, respectively.

15. A computer program product of analyzing data sets obtained from a sample over time, the computer program product comprising computer program code embodied in a computer readable medium, the computer program code comprising program code configured to carry out the method of claim 14.

16. A computer system configured to carry out the method of claim 14.

17. A system for analyzing three dimensional data sets obtained from a sample over time, comprising:
a data set acquisition module configured to obtain a first three dimensional data set from the sample at a first time and a second three dimensional data set from the sample at a second time, different from the first time;
a volume intensity projection (VIP) module configured to create a first volume intensity projection (VIP) image from the first three dimensional data set and a second VIP image from the second three dimensional data set;
a registration module configured to identify and register at least one first landmark in the first VIP image and the at least one first landmark in the second VIP image; and
an alignment module configured to align the first and second VIP images based on the registered at least one first landmark in the first and second VIP images.

18. The system of claim 17:
wherein the registration module is further configured to register at least one subject area in the first three dimensional data set; and
wherein the alignment module is further configured to align the first and second VIP images based on the registered at least one first landmark to locate the registered subject area of the first three dimensional data set in the second three dimensional data set so as to allow comparison of the registered subject area in the first and second VIP at the respective first and the second times.

19. The system of claim 18, further comprising a comparison module configured to:
measure an attribute of the registered subject area of the first three dimensional data set;
measure an attribute of the located subject area of the second three dimensional data set; and
compare the measured attributes of the registered and located subject areas so as to allow comparison of the subject areas at the first and second times.

20. The system of claim 17, wherein the first and second three dimensional data sets are optical coherence tomography (OCT) data sets.

21. The system of claim 17, further comprising:
a rotation module configured to rotate the second three dimensional data set to align an axis of the second three dimensional data set with an axis of the first three dimensional data set to obtain a rotated three dimensional data set, wherein the VIP module is further configured to create a rotated VIP image based on the rotated three dimensional data set.

22. The system of claim 21:
wherein the registration module is further configured to register at least one subject area in the first three dimensional data set and identify and register the at least one first landmark on the rotated VIP image; and
wherein the alignment module is further configured to align the first and rotated VIP images based on the registered at least one first landmark in the first and rotated VIP image and align the first and rotated VIP images based on the registered at least one first landmark to locate the registered subject area in the first three dimensional data set in the rotated three dimensional data set so as to allow comparison of the registered subject area and the located subject area of the first and rotated three dimensional data sets, respectively.

23. The system of claim 22, further comprising a comparison module configured to:
measure an attribute of the registered subject area of the first three dimensional data set;
measure an attribute of the located subject area of the rotated three dimensional data set; and
compare the measured attributes of the registered and located subject areas so as to allow comparison of the subject areas in the first and rotated three dimensional data sets.

24. A computer program product for analyzing three dimensional data sets obtained from a sample over time, the computer program product comprising:
computer readable storage medium having computer readable program code embodied in said medium, the computer readable program code comprising:
computer readable program code configured to obtain a first three dimensional data set from the sample at a first time;
computer readable program code configured to create a first volume intensity projection (VIP) image from the first three dimensional data set;
computer readable program code configured to identify and register at least one first landmark in the first VIP image;
computer readable program code configured to obtain a second three dimensional data set from the sample at a second time, different from the first time;
computer readable program code configured to create a second VIP image from the second three dimensional data set;
computer readable program code configured to identify and register the at least one first landmark in the second VIP image; and
computer readable program code configured to align the first and second VIP images based on the registered at least one first landmark in the first and second VIP images.

25. The computer program product of claim 24, further comprising computer readable program code configured to register at least one subject area in the first three dimensional data set, wherein the computer readable program code configured to align further comprises computer readable program code configured to align the first and second VIP images based on the registered at least one first landmark to locate the registered subject area of the first three dimensional data set in the second three dimensional data set so as to allow comparison of the registered subject area in the first and second three dimensional data sets at the respective first and the second times.

26. The computer program product of claim 25, further comprising:
computer readable program code configured to measure an attribute of the registered subject area of the first three dimensional data set;
computer readable program code configured to measure an attribute of the located subject area of the second three dimensional data set; and
computer readable program code configured to compare the measured attributes of the registered and located subject areas so as to allow comparison of the subject areas at the first and second times.

27. The computer program product of claim 24, wherein the first and second three dimensional data sets are optical coherence tomography (OCT) data sets.

28. The computer program product of claim 24, further comprising:
computer readable program code configured to rotate the second three dimensional data set to align an axis of the second three dimensional data set with an axis of the first three dimensional data set to obtain a rotated three dimensional data set; and
computer readable program code configured to create a rotated VIP image based on the rotated three dimensional data set.

29. The computer program product of claim 28, further comprising:
computer readable program code configured to register at least one subject area in the first three dimensional data set,
computer readable program code configured to identify and register the at least one first landmark on the rotated VIP image; and
computer readable program code configured to align the first and rotated VIP images based on the registered at least one first landmark in the first and rotated VIP images and align the first and rotated VIP images based on the registered at least one first landmark to locate the registered subject area in the first three dimensional data set in the rotated three dimensional data set so as to allow comparison of the registered subject area and the located subject area of the first and rotated three dimensional data sets, respectively.

30. The computer program product of claim 29, further comprising:
computer readable program code configured to measure an attribute of the registered subject area of the first three dimensional data set;
computer readable program code configured to measure an attribute of the located subject area of the rotated three dimensional data set; and
computer readable program code configured to compare the measured attributes of the registered and located subject areas so as to allow comparison of the subject areas in the first and rotated three dimensional data sets.

31. A method for analyzing three dimensional data sets obtained from a sample over time, comprising:
obtaining a first three dimensional data set from the sample at a first time;
creating a first volume intensity projection (VIP) image from the first three dimensional data set;
identifying and registering at least one first landmark on the first VIP image;

registering a subject area in the first three dimensional data set on the first VIP image;

obtaining a second three dimensional data set at a second time, different from the first time;

creating a second VIP image from the second three dimensional data set;

identifying and registering the at least one first landmark on the second VIP image;

deriving alignment between the first at least one landmark registered on first VIP and second VIP images; and locating the subject area registered in the first three dimensional data set in the second three dimensional data set based on registration of the at least one landmark derived from the first three dimensional data set and alignment between the first and second VIP images.

32. The method of claim 31 further comprising:

measuring an attribute of the registered subject area in the first three dimensional data set obtained at the first time;

measuring an attribute of the located subject area in the second data set obtained at the second time; and comparing the attributes of the registered and located subject areas so as to allow comparison of the subject areas at the first and second times.

33. The method of claim 32, further comprising:

rotating the second three dimensional data set to align an axis of the second three dimensional data set with an axis of the first three dimensional data set to provide a rotated three dimensional data set;

creating a rotated VIP image from the rotated three dimensional data set;

identifying and registering the at least one landmark on the rotated VIP image;

deriving alignment between the at least one landmark on the first and rotated VIP images; and locating the subject area registered in the first three dimensional data set in the rotated three dimensional data set based on registration of the at least one landmark derived from the first three dimensional data set and alignment between the first and rotated VIP images.

34. The method of claim 33 further comprising:

measuring an attribute of the registered subject area in the first three dimensional data set;

measuring an attribute of the located subject area in the rotated three dimensional data set; and comparing the attributes of the registered and located subject areas in the first and rotated data sets.

35. The method of claim 31 further comprising:

rotating the first three dimensional data set about an axis;

interpolating the rotated first three dimensional data set to a regular grid;

creating a rotated VIP image from the rotated first three dimensional data set;

identifying and registering at least one second landmark on rotated VIP image;

registering a second subject area in the rotated three dimensional data set to landmark on rotated VIP image;

obtaining a third three dimensional data set at a third time, different from the first and second times;

rotating and aligning orientation of the third three dimensional data set to the first rotated three dimensional data set;

creating a third VIP image from the rotated and aligned third three dimensional data set;

identifying and registering the at least one second landmark on the third VIP image;

deriving alignment between the second at least one landmark registered on rotated VIP and third VIP images; and locating the subject area registered in the rotated three dimensional data set in the third three dimensional data set based on registration of the at least one second landmark derived from the rotated three dimensional data set and alignment between the rotated and third VIP images.

36. The method of claim 35 further comprising:

measuring an attribute of the registered subject area in the rotated three dimensional data set;

measuring an attribute of the located subject area in the third three dimensional data set; and comparing the attributes of the registered and located subject areas of the rotated and third data sets, respectively.

37. The method of claim 31, wherein the first three dimensional data set is rotated about an axis to provide a rotated first three dimensional data set, wherein the first VIP image is created from the rotated first three dimensional data set, wherein the second three dimensional data set is rotated about an axis aligned with the rotated first three dimensional data set to provide a rotated second three dimensional data set and wherein the second VIP image is created from the rotated second three dimensional data set.

38. The method of claim 37, further comprising:

measuring an attribute of the registered subject area in the first rotated three dimensional data set;

measuring an attribute of the located subject area in the second three dimensional data set; and comparing the attributes of the registered and located subject areas of the rotated first and second data sets, respectively.

* * * * *

UNITED STATES PATENT AND TRADEMARK OFFICE
CERTIFICATE OF CORRECTION

| | | |
|---|---|---|
| PATENT NO. | : 7,869,663 B2 | |
| APPLICATION NO. | : 11/461083 | |
| DATED | : January 11, 2011 | |
| INVENTOR(S) | : Buckland et al. | |

It is certified that error appears in the above-identified patent and that said Letters Patent is hereby corrected as shown below:

In the Specification:
Column 2, Line 24:  Please correct "In her embodiments"
                         to read -- In further embodiments --

Signed and Sealed this
Fifth Day of July, 2011

David J. Kappos
*Director of the United States Patent and Trademark Office*